United States Patent
Geppetti

(10) Patent No.: US 8,492,396 B2
(45) Date of Patent: Jul. 23, 2013

(54) THERAPEUTIC USES OF ADRENERGIC α-1 RECEPTOR ANTAGONISTS

(75) Inventor: Pierangelo Geppetti, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 12/730,559

(22) Filed: Mar. 24, 2010

(65) Prior Publication Data

US 2011/0009436 A1 Jan. 13, 2011

Related U.S. Application Data

(63) Continuation of application No. PCT/IB2008/003126, filed on Sep. 24, 2008.

(60) Provisional application No. 60/975,324, filed on Sep. 26, 2007.

(30) Foreign Application Priority Data

Sep. 26, 2007 (EP) .................... 07291148

(51) Int. Cl.
*A01N 43/66* (2006.01)
*A61K 31/53* (2006.01)

(52) U.S. Cl.
USPC .................................. 514/266.24

(58) Field of Classification Search
USPC .................................. 514/266.24
See application file for complete search history.

(56) References Cited

U.S. PATENT DOCUMENTS

| | | | | |
|---|---|---|---|---|
| 4,661,491 | A * | 4/1987 | Regnier | 514/266.24 |
| 5,985,914 | A * | 11/1999 | Zeldis et al. | 514/455 |
| 2002/0198136 | A1 | 12/2002 | Mak et al. | |
| 2003/0060513 | A1* | 3/2003 | Arneric et al. | 514/648 |
| 2005/0187222 | A1 | 8/2005 | Garvey et al. | |
| 2007/0093493 | A1 | 4/2007 | Denes et al. | |

FOREIGN PATENT DOCUMENTS

WO WO 2004/017960 A1 3/2004

OTHER PUBLICATIONS

Bremnor et al American Family Physician (2002) 65(8) 1589-1595.*
www.sclero.org (1998), 2 pages.*
http://www.health.harvard.edu/newsweek/Diagnosing_and_treating_interstitial_cystitis.htm (2000), 3pages.*
Siroky (Reviews of Urology 6(1) 2004, p. S3-S7.*
Treatment Guidelines, Interstitial Cystitis Association, May 2005, Retrieved from the Internet: URL: http://www.ichelp.org/PatientInformation/TreatmentOptions/TreatmentGuidelines/tabid/85/Default.aspx [retrieved on Dec. 7, 2007].
DeNunzio et al, The Evolution of Detrusor Overactivity After Watchful Waiting, Medical Therapy and Surgery in Patients with Bladder Outlet Obstruction, J Urology, 2003 (169) pp. 535-539.
Feldman et al, beta-Adrenergic Receptor-Mediated Suppression of Interleukin 2 Receptors in Human Lymphoctes, J Immunology, 1987 (139) 10 pp. 3355-3359.
Kaplan et al, Combination of Alfuzosin and Sildenafil is Superior to Monotherapy in Treating Lower Urinary Tract Synmptoms and Erectile Dysfunction, European Urology, 2007 (51) pp. 1717-1723.
Kinnman et al, Involvement of the Sympathetic Postganglionic Neuron in Capsaicin-Induced Secondary Hyperalgesia in the Rat, Neuroscience, 1995 (65) 1 pp. 283-291.
Lin et al, Sympathetic Modulation of Acute Cutaneous Flare Induced by Intradermal Injection of Capsaicin in Anesthetized Rats, J Neurophysiol, 2003 (89) pp. 853-861.
Madden et al, Catecholamine Influences and Sympathetic Neural Modulation of Immune Responsiveness, Annu. Rev. Pharmacol. Toxicol., 1995 (35) pp. 417-448.
Maestroni, Dendritic Cell Migration Controlled by alphalb-Adrenergic Receptors, J Immunology, 2000 (165) pp. 6743-6747.
Maggi et al, Cyclophosphamide Cystitis in Rats: Involvement of Capsaicin-sensitive Primary Afferents, J Auton Nerv Syst., 1992 (38) pp. 201-208.
Rigoni et al, Neurogenic Responses Mediated by Vanilloid Receptor—(TRPV1) are Blocked by the High Affinity Antagonist, Iodo-Resiniferatoxin, Br J Pharmacol., 2003 (138) pp. 977-985.
Zou et al, The Effects of Sympathectomy on Capsaicin-evoked fos Expression of Spinal Dorsal Horn GABAergic Neurons, Brain Research, 2002 (958) pp. 322-329.

* cited by examiner

*Primary Examiner* — Shirley V Gembeh
(74) *Attorney, Agent, or Firm* — Scully, Scott, Murphy & Presser, P.C.

(57) ABSTRACT

The disclosure relates to methods of using an adrenergic α-1 receptor antagonist or its pharmaceutically acceptable salts for treating and/or preventing interstitial cystitis, overactive bladder or detrusor overactivity.

3 Claims, No Drawings

THERAPEUTIC USES OF ADRENERGIC α-1 RECEPTOR ANTAGONISTS

Alfuzosine is a known adrenergic α-1 receptor antagonist that exhibits interesting muscle relaxant properties. Its use as an anti-hypertensive agent was largely reported and it is currently administered for the treatment of the benign prostatic hyperplasia (BPH), also known as nodular hyperplasia, benign prostatic hypertrophy or benign enlargement of the prostate (BEP). Alfuzosine is also indicated in the treatment of the low urinary tract symptoms (LUTS). Although reduction in smooth muscle tone of the bladder-urethral functional unit is considered responsible for the beneficial effects of adrenergic α-1 receptor antagonists, various reports suggest that amelioration of storage LUTS cannot solely originate from the reduction of bladder outlet resistance.

Neuropeptides release from peripheral endings causes a series of inflammatory responses commonly referred to as neurogenic inflammation. This inflammatory response include at the vascular level arteriolar vasodilatation (flare in the skin) and plasma protein extravasation and other tissue specific responses as smooth muscle contraction of urinary bladder, bronchi etc. Neurogenic inflammation is considered to play a major role in different diseases of the urinary tract, including cystitis, prostatitis, overactive bladder syndrome (OAB) and detrusor overactivity (Geppetti et al., 1996, *Neurogenic inflammation*. Boca Raton: CRC Press).

The interaction between sympathetic nerves and cells of the immune system has been demonstrated in terms of distribution of tyrosine hydroxylase-positive fibers in lymphoid organs, expression of α-adrenoceptors on cells of the immune system, and immunomodulatory effects of the main sympathetic neurotransmitter noradrenaline (Feldman et al., 1987, *J Immunol*, 139, 3355-9; Madden et al., 1995, *Annu Rev Pharmacol Toxicol*, 35, 417-48). More recent findings show that noradrenaline exerts both a chemotactic and chemokinetic activity on immature dendritic cells and enhances spontaneous emigration of dendritic cells from skin explants. All these effects are blocked by α1-adrenoceptors antagonists (Maestroni, 2000, *J Immunol*, 165, 6743-7).

Sympathetic afferents are known to modulate neurogenic inflammatory responses by interaction with primary afferent terminals. Sympathectomy results in the reduction of C-fos expression in dorsal horn neurons induced by capsaicin (Zou et al., 2002, *Brain Res*, 958, 322-9) and hyperalgesia induced by intradermal capsaicin is blocked by an α1-adrenoceptor antagonist (Kinnman et al., 1995, *Neuroscience*, 65, 283-91). More recently, it has been shown that capsaicin-induced flare in the rat skin was reduced by an α1-adrenoceptor antagonist but not by a α2-adrenoceptor antagonist (Lin et al., 2003, *J Neurophysiol*, 89, 853-61). These studies suggest that intact sympathetic efferents modulate neurogenic inflammation in the skin and that peripheral α1-adrenoceptors play a major role in this modulation.

Nevertheless, the use of adrenergic α-1 receptor antagonists for treating "irritative" disorders of the urinary tract such as interstitial cystitis, overactive bladder or detrusor overactivity has not been suggested so far.

Interstitial cystitis (IC) or inflammatory bladder is a chronic inflammatory condition of the bladder. Unlike common cystitis, also known as urinary tract infection, IC is believed not to be caused by bacteria and does not respond to conventional antibiotic therapy. Its cause is not ascertained and there is currently no cure for IC. Symptoms include frequency and/or urgency to urinate and pain.

Overactive bladder syndrome (sometimes called an 'irritable' bladder or 'detrusor instability') and detrusor overactivity are common conditions characterized by repeated and uncontrolled bladder contractions. Symptoms include urgency, frequency, nocturia and urge incontinence. Their causes are not fully understood although they are partially due to the defective behaviour of the detrusor. Bladder training is usually the main treatment, and medication (including antimuscarinic agents) does generally not alleviate all symptoms.

It is therefore highly desirable to provide new medicines for the treatment and/or prevention of the above disorders.

According to a first object, the present invention provides for the use of an adrenergic α-1 receptor antagonist or its pharmaceutically acceptable salts for the preparation of a medicament for treating and/or preventing inflammatory bladder, overactive bladder or detrusor overactivity.

Preferably, said inflammatory bladder results from or is associated with interstitial cystitis. According to a preferred aspect, the present invention provides for the use of an adrenergic α-1 receptor antagonist or its pharmaceutically acceptable salts for the preparation of a medicament for treating and/or preventing interstitial cystitis.

According to a preferred aspect, said adrenergic α-1 receptor antagonist is alfuzosine or its pharmaceutically acceptable salts, more preferably alfuzosine hydrochloride.

For the uses of the invention, an effective amount of said adrenergic α-1 receptor antagonist, or of a pharmaceutically acceptable salt or solvate thereof, is administered to the patients who require such a treatment. Preferably, said patients are male patients.

Said adrenergic α-1 receptor antagonist above, and the pharmaceutically acceptable salts and solvates thereof, may be used at daily doses of 0.01 to 20 mg per kilo of body weight of the mammal to be treated, preferably at daily doses of from 0.1 to 10 mg/kg. In humans, the dose may vary preferably from 0.5 mg to 1500 mg per day, in particular from 2.5 to 500 mg, depending on the age of the individual to be treated, the type of treatment, prophylactic or curative, and the seriousness of the disorder. Said adrenergic α-1 receptor antagonists are generally administered as a dosage unit of 0.1 to 500 mg, preferably of 0.5 to 100 mg, of active principle, one to five times a day. Preferable unit dosage forms comprise 2.5 or 10 mg of alfuzosine hydrochloride.

Said dosage units are preferably formulated in pharmaceutical compositions in which the active principle is mixed with a pharmaceutical excipient.

In the pharmaceutical compositions of the present invention for oral, sublingual, subcutaneous, intramuscular, intravenous, topical, transdermal or rectal administration, said adrenergic α-1 receptor antagonists, and the pharmaceutically acceptable salts and solvates thereof, may be administered in unit administration forms, mixed with conventional pharmaceutical supports, to animals and humans for treating the abovementioned disorders. The unit administration forms which are suitable comprise oral forms such as tablets, gel capsules, powders, granules and oral solutions or suspensions, sublingual and buccal administration forms, subcutaneous, intramuscular or intravenous administration forms, local administration forms and rectal administration forms.

When a solid composition in the form of tablets is prepared, the main active ingredient is mixed with a pharmaceutical vehicle such as gelatin, starch, lactose, magnesium stearate, talc, gum arabic or the like. The tablets may be coated with sucrose or other suitable materials, or they may be treated such that they have sustained or delayed activity and that they release, in a continuous manner, a predetermined amount of active principle. Usual excipients include lactose monohydrate, microcrystalline cellulose, povidone, sodium carboxymethylstarch, magnesium stearate, ethylcellulose, hypromellose, macrogol 400, and titane dioxide.

A preparation of gel capsules is obtained by mixing the active ingredient with a diluent and pouring the mixture obtained into soft or hard gel capsules.

A preparation in the form of a syrup or elixir may contain the active ingredient together with a sweetener, preferably a calorie-free sweetener, methylparaben and propylparaben as antiseptics, and also a flavour enhancer and a suitable colorant.

The water-dispersible powders or granules may contain the active ingredient mixed with dispersing agents or wetting agents, or suspending agents, such as polyvinylpyrrolidone, and also with sweeteners or flavour correctors.

For local administration, the active principle is mixed into an excipient for preparing creams or ointments, or it is dissolved in a vehicle for intraocular administration, for example in the form of an eyewash.

For rectal administration, use is made of suppositories prepared with binders which melt at rectal temperature, for example cocoa butter or polyethylene glycols.

For parenteral administration, aqueous suspensions, saline solutions or injectable sterile solutions which contain pharmacologically compatible dispersion agents and/or wetting agents, for example propylene glycol or butylene glycol, are used.

The active principle may also be formulated in the form of microcapsules, optionally with one or more supports or additives.

The following examples further illustrate the present invention:

EXAMPLES

In vivo Assay

Male Sprague-Dawley rats and Swiss mice were administered with CYP (150 mg/kg, i.p.) or its vehicle (0.9% NaCl) for cystitis induction. 48 hours later urinary bladders were removed and placed in an organ bath for motor response measurement. Writhing behaviors and plasma protein extravasation were investigated 90 min after the CYP administration.

Isolated Strips of Rat Urinary Bladder

Strips of rat urinary bladder were taken from terminally anesthetized animals and mounted in organ baths and after an equilibration period the eNANC contractile response to electrical field stimulation (EFS, 5 Hz, 1 ms width, 10 V) in the absence and presence of atropine (1 µM) is studied (Rigoni et al., 2003, Br J Pharmacol, 138, 977-85) The contraction produced by EFS in these experimental conditions is entirely mediated by SP and NKA released from terminals of primary sensory neurons. The eNANC response to EFS was reproducible at 60 min intervals. The effect of alfuzosin or its vehicle on the eNANC response to EFS was studied in parallel experiments. At the beginning or end of each experiment tissues were challenged with carbachol (1 µM). The effect of alfuzosin was studied also in bladder strips obtained from rats treated with cyclophosphamide.

Drug Administration

Intraperitoneal administration of cyclophosphamide (150 mg/kg, 48 h before) is known to decrease bladder capacity and increased micturition frequency (Maggi et al., 1992, J Auton Nerv Syst, 38, 201-8). These effects of cyclophosphamide were abolished in rats pretreated with capsaicin as adults (Maggi et al., 1992, J Auton Nerv Syst, 38, 201-8). Thus, the inflammatory responses to cyclophosphamide are mediated by neurogenic inflammatory mechanisms.

Plasma Extravasation

Evans blue dye was used to measure plasma extravasation. The proinflammatory stimulus was given immediately after the injection of the dye (30 mg/kg i.v. over 5 s) in the jugular vein. The chest was opened 10 min or at different time intervals as required after the injection of Evans blue and the animal perfused for 3 min with a phosphate buffer. The urinary bladder, urethra and prostate were removed, blotted and weighed. The tissue was then placed in 3 ml of formamide at 50° C. for 18 hr to extract the extravasated Evans blue dye. The amount of Evans blue extravasated from the trachea and bronchi was measured using a spectrophotometer and expressed as ng/mg of wet weight.

Results shown that CYP-evoked plasma protein extravasation in urinary bladder was completely prevented by two putative TRPA1 antagonist, ruthenium red (4 mg/kg, s.c.) and camphor (50 µmol/kg i.p.).

In addition, in isolated urinary bladder strips, the contractile response to electrical field stimulation in the presence of atropine (eNANC) was reduced in urinary bladders taken from CYP-treated rats as compared to bladders from vehicle-treated rats.

Intravenous alfuzosin pretreatment (30 µg/kg) restored (>50% of reversal) the normal response to EFS.

Similarly, the contractile response to capsaicin was reduced in urinary bladder taken from CYP-treated rats, was partially restored by pretreatment with alfuzosin (~50% of reversal). In contrast, the response to carbachol or SP were not affected by in vivo CYP administration. Finally, the number of writhings evoked in mice by intraperitoneal injection of acetic acid (10.3±0.6) was increased by ~50% by CYP administration, an effect that was significantly inhibited by pre-treatment alfuzosin (30 µg/kg, i.v., 48% of reduction).

It was thus confirmed in vivo that the ability of CYP to activate sensory nerve terminal inducing urinary bladder inflammation is mediated by TRPA1 activation. This inflammatory mechanism may result in the depletion of proinflammatory neuropeptides. Blockade of the $\alpha_1$-adrenergic receptor on sensory terminals regulates this phenomenon preventing the inflammatory response and neuropeptide depletion $\alpha_1$-adrenoreceptor blockade by alfuzosin also inhibits nociceptor sensitization induced by CYP treatment. These results offer a mechanistic explanation to the use of alfuzosin in the treatment of different conditions of the lower urinary tract characterized by irritation and pain symptoms.

Pharmaceutical Composition According to the Invention

As a representative example, a unitary dosage form of a compound of the invention in the form of a tablet may comprise the following constituents:

| | |
|---|---|
| Alfuzosine hydrochloride | 5 mg |
| Lactose | 122 mg |
| Microcrystalline cellulose | 36.0 mg |
| Sodium carboxymethylstarch | 7.0 mg |
| Polyvidone | 9 mg |
| Magnesium stearate | 1.0 mg |

What is claimed is:

1. A method for treating interstitial cystitis comprising administering to a patient in need thereof an effective amount of alfusozine or a pharmaceutically acceptable salt thereof, as the sole active ingredient.

2. The method according to claim 1, wherein said pharmaceutically acceptable salt is alfuzosine hydrochloride.

3. The method according to claim 1, wherein the patient is male.

\* \* \* \* \*